United States Patent [19]

Johnson et al.

[11] Patent Number: 5,585,318
[45] Date of Patent: *Dec. 17, 1996

[54] ALKYNE HYDROGENATION PROCESS

[75] Inventors: Marvin M. Johnson; Tin-Tack P. Cheung, Bartlesville, both of Okla.

[73] Assignee: Phillips Petroleum Company, Bartlesville, Okla.

[*] Notice: The term of this patent shall not extend beyond the expiration date of Pat. No. 5,489,565.

[21] Appl. No.: 560,607

[22] Filed: Nov. 20, 1995

Related U.S. Application Data

[62] Division of Ser. No. 376,178, Jan. 20, 1995.

[51] Int. Cl.$^6$ .................................................. B01J 23/58
[52] U.S. Cl. ........................................... 502/330; 502/325
[58] Field of Search ..................................... 502/330, 325

[56] References Cited

U.S. PATENT DOCUMENTS

| | | | |
|---|---|---|---|
| 3,325,556 | 6/1967 | Rosset | 260/677 |
| 3,932,548 | 1/1976 | Raush | 260/668 D |
| 4,009,126 | 2/1977 | McFarland | 252/473 |
| 4,131,743 | 12/1978 | Yoshida et al. | 560/244 |
| 4,321,409 | 3/1982 | Yoshida et al. | 560/244 |
| 4,404,124 | 9/1983 | Johnson et al. | 252/466 PT |
| 4,644,088 | 2/1987 | McFarland | 585/658 |
| 4,658,080 | 4/1987 | McFarland | 585/658 |
| 5,489,565 | 2/1996 | Cheung et al. | 502/325 |

OTHER PUBLICATIONS

Yeung H. Park and Geoffrey L. Price, "Promotional Effects of Potassium on Pd/Al$_2$O$_3$ Selective Hydrogenation Catalysts", Ind. Eng. Chem. Res., vol. 31, No. 2, pp. 469–474 Feb. 1992.

Primary Examiner—Helane Myers
Assistant Examiner—Alexander G. Ghyka
Attorney, Agent, or Firm—Karl K. Brandes

[57] ABSTRACT

$C_2$–$C_6$ alkynes (preferably acetylene) contained in feeds which also contain sulfur impurities are hydrogenated to the corresponding alkenes in the presence of a supported palladium catalyst which has been promoted with alkali metal fluoride (preferably potassium fluoride). A specific catalyst consists essentially of a palladium component, at least one alkali metal fluoride (preferably KF) and an inorganic support material (preferably alumina).

20 Claims, No Drawings

ALKYNE HYDROGENATION PROCESS

This application is a division of U.S. patent application Ser. No. 08/376,178, filed Jan. 20, 1995.

BACKGROUND OF THE INVENTION

This invention relates to a process for catalytically hydrogenating alkyne-containing feeds which also comprise sulfur impurities.

The selective hydrogenation of alkynes, which generally are present in small amounts in alkene-containing streams (e.g., acetylene contained in ethylene streams from thermal ethane crackers), is commercially carried out in the presence of alumina-supported palladium catalysts. In the case of the selective hydrogenation of acetylene to ethylene, preferably an alumina-supported palladium/silver catalyst is used in accordance with the disclosure in U.S. Pat. No. 4,404,124 and its division, U.S. Pat. No. 4,484,015. The operating temperature for this hydrogenation process is selected such that essentially all acetylene is hydrogenated to ethylene (and thus removed from the feed stream) while only an insignificant amount of ethylene is hydrogenated to ethane (to minimize ethylene losses and to avoid a "runaway" reaction which is difficult to control, as has been pointed out in the above-identified patents).

It is generally known by those skilled in the art that sulfur impurities (such as $H_2S$, COS, mercaptans and organic sulfides) when present in alkyne-containing feeds can poison and deactivate these palladium-containing catalysts. The present invention is directed to the use of an improved palladium catalyst in the selective hydrogenation alkynes to alkene, in particular of acetylene to ethylene, in the presence of sulfur-containing impurities.

SUMMARY OF THE INVENTION

It is an object of this invention to carry out the selective hydrogenation of $C_2$–$C_6$ alkyne(s) to the corresponding alkene(s) in the presence of sulfur impurities employing an improved palladium-containing catalyst. It is a particular object of this invention to carry out the selective hydrogenation of acetylene to ethylene in the presence of sulfur compounds. Other objects and advantages will be apparent from the detailed description and appended claims.

In accordance with this invention, a process for selectively hydrogenating at least one alkyne containing 2–6 carbon atoms per molecule, which is present in a feed also comprising at least one sulfur compound, with hydrogen gas to at least one corresponding alkene containing 2–6 carbon atoms per molecule comprises contacting said feed and said hydrogen gas with a catalyst which comprises palladium, at least one alkali metal fluoride and an inorganic support material.

Preferably, the catalyst also comprises silver. The presently preferred alkali metal fluoride is potassium fluoride. Preferably, the at least one alkyne is acetylene (ethyne) and the at least one alkene is ethylene (ethene).

DETAILED DESCRIPTION OF THE INVENTION

The catalyst which is employed in the selective hydrogenation process of this invention can be any supported palladium catalyst composition which also comprises at least one alkali metal fluoride, preferably potassium fluoride. Preferably, silver is also present in the catalyst composition. This catalyst composition can be fresh or it can be a used and thereafter oxidatively regenerated catalyst composition. This catalyst can contain any suitable inorganic solid support material. Preferably, the inorganic support material is selected from the group consisting of alumina, titania, zirconia, and mixtures thereof. The presently more preferred support material is alumina, most preferably alpha-alumina. This catalyst generally contains about 0.01–1 (preferably about 0.01–0.2) weight-% palladium and about 0.05–1.5 (preferably about 0.1–0.4) weight-% fluorine (chemically bound as alkali metal fluoride), preferably at a F:Pd weight ratio of about 3:1 to about 30:1. Preferably, about 0.01–10 (more preferably about 0.02–2) weight-% silver is also present in the catalyst. Preferably, the Ag:Pd weight ratio in the catalyst is about 2:1 to about 10:1. Particles of this catalyst generally have a size of about 1–10 mm (preferably about 2–6 mm) and can have any suitable shape (preferably spherical or cylindrical). Generally, the surface area of this catalyst (determined by the BET method employing $N_2$) is about 1–100 $m^2/g$.

The above-described catalyst which is employed in the hydrogenation process of this invention can be prepared by any suitable, effective method. The alkali metal fluoride can be incorporated (e.g., by impregnation or spraying) into the support material before it is impregnated with a suitable Pd compound, and preferably also with a suitable Ag compound. Or the alkali metal fluoride can be incorporated (e.g., by impregnation or spraying) into the catalyst simultaneously with or after the impregnation with a suitable Pd compound. When silver is also present in the catalyst composition, the alkali metal compound can be incorporated between the Pd and Ag impregnation steps or after the impregnation with Pd and Ag compounds. The presently preferred catalyst preparation comprises the impregnation of a Pd/Ag/$Al_2O_3$ catalyst material (more preferably the "skin" catalyst obtained by the method described in U.S. Pat. Nos. 4,404,124 and 4,484,015) with an aqueous solution of potassium fluoride (KF), followed by drying and calcining (preferably in air at a temperature of about 300°–450° C., more preferably about 350°–400° C., generally for about 1–10 hours). It is possible, but presently not preferred, to apply a "wet reducing" step (i.e., treatment with dissolved reducing agents such as hydrazine, alkali metal borohydrides, aldehydes such as formaldehyde, carboxylic acids such as forming acid or ascorbic acid, reducing sugars such as dextrose, and the like).

The thus-prepared catalyst composition which has been dried (and preferably also calcined, as described above) can then be employed in the process of this invention for hydrogenating at least one $C_2$–$C_6$ alkyne, preferably acetylene, to at least one corresponding alkene in the presence of at least one sulfur compound. Optionally, the catalyst is first contacted, prior to the alkyne hydrogenation, with hydrogen gas or with gaseous hydrocarbon generally at a temperature in the range of about 30° C. to about 100 ° C., for a time period of about 4 to about 20 hours. During this contacting with $H_2$ or hydrocarbon(s) before the selective alkyne hydrogenation commences, palladium and silver compounds (primarily oxides) which may be present in the catalyst composition after the drying step and the optional calcining step (described above) are substantially reduced to palladium and silver metal. When this optional reducing step is not carried out, the hydrogen gas present in the reaction mixture accomplishes this reduction of oxides of Pd and Ag during the initial phase of the alkyne hydrogenation reaction of this invention.

The selective hydrogenation process of this invention is carried out by contacting (a) a feed gas which comprises at least one $C_2$–$C_6$ alkyne (preferably a $C_2$–$C_6$ alkene stream containing said at least one alkyne as an impurity, generally at a level of about 1 ppm by weight to about 50,000 ppm by weight alkyne) and at least one sulfur compound and (b) hydrogen gas with (c) the catalyst composition which comprises Pd, Ag, at least one alkali metal fluoride and an inorganic support material. Preferred feed alkynes include acetylene, propyne, butyne-1, butyne-2 and mixtures thereof. Particularly preferred is acetylene. These alkynes are primarily hydrogenated to the corresponding alkenes, i.e., acetylene is primarily hydrogenated to ethylene, propyne is primarily hydrogenated to propylene, and the butynes are primarily hydrogenated to the corresponding butenes (butene-1, butene-2). In order to best attain substantially complete removal of the alkyne(s), there should be at least one mole of hydrogen for each mole of alkyne present. Gases (a) and (b) are generally premixed before their contact with the catalyst composition (c).

Suitable sulfur compounds which are present in the feed include (but are not limited to) hydrogen sulfide, carbonyl sulfide (COS), mercaptans (RSH), organic sulfides (R-S-R), organic disulfides (R-S-S-R) and the like, and mixtures thereof, wherein each R can be an alkyl or cycloalkyl or aryl group containing 1–10 carbon atoms. It is within the scope of this invention to have additional compounds (such as methane, ethane, propane, butane, carbon monoxide, water, alcohols, ethers, ketones, carboxylic acids, esters and other oxygenated compounds) present in the feed gas, as long as they do not significantly interfere with the selective hydrogenation of alkyne(s) to alkene(s). Generally, the sulfur compounds are present in the feed gas in trace amounts, preferably at a level of less than about 1 weight percent sulfur, and preferably at a level of about 1–1,000 ppm by weight sulfur (i.e., about 1–1,000 parts by weight S per million parts by weight feed).

The temperature necessary for the selective hydrogenation of alkyne(s) to alkene(s) depends largely upon the activity and selectivity of the catalysts, the amounts of sulfur impurities in the feed, and the desired extent of alkyne removal. Generally, a reaction temperature in the range of about 40° C. to about 200° C. is employed. Preferably, the reaction temperature is about 60°–150° C. Any suitable reaction pressure can be employed. Generally, the total pressure is in the range of about 100 to about 1,000 pounds per square inch gauge (psig). The gas hourly space velocity (GHSV) of the hydrocarbon feed gas can also vary over a wide range. Typically, the space velocity will be in the range of about 1,000 to about 10,000 $m^3$ of feed per $m^3$ of catalyst per hour, more preferably about 2,000 to about 8,000 $m^3/m^3/$ hour. The GHSV of the hydrogen gas stream is chosen so as to provide a molar ratio of $H_2$ to said at least an alkyne in the range of about 0.5:1 to about 100:1, preferably about 1:1 to about 50:1.

Regeneration of the catalyst composition can be accomplished by heating the catalyst composition in air (at a temperature which preferably does not exceed about 700° C.) so as to burn off any sulfur compounds, organic matter and/or char that may have accumulated on the catalyst composition. Optionally, the oxidatively regenerated composition is reduced with $H_2$ or a suitable hydrocarbon (as has been described above) before its redeployment in the selective alkyne hydrogenation of this invention.

The following examples are presented to further illustrate this invention and are not to be construed as unduly limiting its scope.

EXAMPLE I

This example illustrates the preparation of supported, potassium-promoted palladium catalysts (to be used for acetylene hydrogenation).

Catalyst A (Control) was a commercial Pd/Ag/$Al_2O_3$ catalyst which contained 0.023 weight-% Pd, 0.065 weight-% Ag and about 99 weight-% alumina. It had a BET/$N_2$ surface area of 3–5 $m^2$/g, and had been prepared substantially in accordance with the method described in U.S. Pat. No. 4,404,124 (column 4, lines 32–45). Catalyst A had been provided by United Catalysts Inc. (UCI), Louisville, Ky., under the product designation of "G-83C".

Catalyst B (Control) was prepared by soaking 70.8 grams of Catalyst A in a solution of 0.51 gram KOH in 21.9 grams of distilled water for 1 hour. The thus-impregnated catalyst material was dried for 3 hours at 82° C. and then calcined in air for 3 hours at 370° C.

Catalyst C (Invention) was prepared by soaking 70.9 grams of Catalyst A in 100 cc of an aqueous solution containing 10.0 grams KF (potassium fluoride) for 1.5 hours. The thus-impregnated catalyst material washed three times with distilled water, soaked in distilled water overnight, and dried at 82° C. for 2 hours. Thereafter, the catalyst material was soaked again with an aqueous solution containing 0.53 gram KF in 21.5 grams of water for 1.5 hours. The twice-impregnated catalyst material was dried at 82° C. and then calcined in air at 370° C. for 3 hours.

Catalyst D (Control) was prepared by impregnating 23.1 grams of a Pd/$Al_2O_3$ catalyst (containing about 0.02 weight-% Pd, no Ag; provided by UCI under the product designation of "G-83A") with a solution of 0.157 gram KOH in 7.06 grams of distilled water, followed by drying at 82° C. for several hours and calcining in air at 370° C. for 2 hours. Catalyst D contained 0.5 weight-% K.

Catalyst E (Invention) was prepared soaking 23.1 grams of "G-83" (Pd/$Al_2O_3$) in a solution of 4.33 grams of KF in 100 cc $H_2O$ for 3 hours. The supernatant KF solution was decanted, and the KF-treated catalyst material was rinsed several times with distilled water and soaked in 300 cc distilled water overnight, followed by drying at 82° C. for several hours. Thereafter, the catalyst material was impregnated again with an aqueous KF solution containing 0.17 grams KF and 7.1 grams of $H_2O$. The twice impregnated catalyst material was dried at 82° C. for several hours and calcined in air at 340° C. for several hours. Catalyst E contained 0.5 weight-% K.

EXAMPLE II

This example illustrates the poisoning effect of hydrogen sulfide on the performance of two acetylene hydrogenation catalysts (Catalysts B and C).

The selective acetylene hydrogenation tests were carried out as follows. About 20 cc of Catalyst B or Catalyst C was placed into a stainless steel reactor tube having a 0.5 inch inner diameter and a length of about 18 inches. Each catalyst was treated with flowing hydrogen gas under a pressure of 200 psig, at a temperature of about 130°–150 ° F., for about 16 hours. Thereafter, the reactor tube was cooled to about 120 ° F., and a hydrocarbon-containing feed gas containing 27.1 weight-% methane, 15.9 weight-% ethane, 55.3 weight-% ethylene, and 0.30 weight-% acetylene and 1.35 weight-% hydrogen was introduced into the reactor tube at a rate of about 900 cc/minute. The reactor temperature was gradually increased to the desired reaction temperature, and samples of the formed product were analyzed by means of a gas chromatograph at various time intervals.

In order to evaluate the effect of hydrogen sulfide on the two catalysts, nitrogen gas containing about 1 volume-% $H_2S$ was passed over 20 cc of each catalyst placed in the above-described reactor tube, at a flow rate of about 100 cc/minute. The temperature was about 73° F. and the pressure was 1 atm. After $H_2^S$ breakthrough was detected (by means of an aqueous $CdSO_4$ solution which formed yellow CdS precipitate), the flow of the $N_2/H_2S$ gas was stopped. In the case of Catalyst B, $H_2S$ breakthrough was detected after about 650 cc of the $N_2/H_2S$ gas had passed through the reactor, whereas in the case of Catalyst C, $H_2S$ breakthrough occurred after about 350 cc of the $N_2/H_2S$ gas had flowed through the reactor. The reactor tube was then purged for about 20 hours with flowing hydrogen gas (flow rate: about 100 cc/minute) at a temperature of about 200 ° F. and a pressure of about 50 psig. Thereafter, the selective acetylene hydrogenation test (using the above-described hydrocarbon feed gas and the above-described test procedure) was started for each of the $H_2S$-poisoned catalysts. Pertinent test results are summarized in Table I.

TABLE I

| Catalyst | $H_2S$-Poisoned | Reaction Temp. (°F.) | Mol-% Acetylene in Product | Ethylene/Ethane Mol-Ratio in Product |
|---|---|---|---|---|
| B | No | 123 | 0.169 | 3.71 |
|   |    | 139 | 0.087 | 3.72 |
|   |    | 147 | 0.019 | 3.72 |
|   |    | 156 | 0 | 3.71 |
|   |    | 173 | 0 | 3.68 |
|   |    | 207 | 0 | 3.49 |
|   |    | 221 | 0 | 3.32 |
| B | Yes | 204 | 0.120 | 3.71 |
|   |    | 310 | 0.035 | 3.38 |
|   |    | 329 | 0.018 | 3.29 |
|   |    | 360 | 0.011 | 3.19 |
| C | No | 153 | 0.002 | 3.70 |
|   |    | 156 | 0 | 3.70 |
|   |    | 184 | 0 | 3.59 |
|   |    | 229 | 0 | 3.28 |
| C | Yes | 203 | 0.132 | 3.72 |
|   |    | 257 | 0.002 | 3.66 |
|   |    | 264 | 0 | 3.65 |
|   |    | 294 | 0 | 3.60 |
|   |    | 316 | 0 | 3.58 |
|   |    | 339 | 0 | 3.56 |
|   |    | 357 | 0 | 3.52 |
|   |    | 381 | 0 | 3.55 |
|   |    | 418 | 0 | 3.54 |
|   |    | 447 | 0 | 3.53 |

Test results in Table I clearly show that the $H_2S$-poisoned Catalyst B (KOH-promoted Pd/Ag/$Al_2O_3$) was essentially useless as a selective acetylene hydrogenation catalyst because even at temperatures above 300° F., all acetylene had not been completely hydrogenated, while a substantial amount of ethylene had been hydrogenated to ethane (as indicated by a significantly decreased ethylene/ethane ratio). In the case of $H_2S$-poisoned Catalyst C (KF-promoted Pd/Ag/$Al_2O_3$), however, essentially complete acetylene hydrogenation had occurred at about 264° F., while the undesirable hydrogenation of ethylene to ethane occurred only to an insignificant extent; as evidenced by an ethylene/ethane ratio which had decreased only about 2% from the initial value of 3.72. Even at a relatively high temperature of 447° F., this ratio had decreased only about 5%.

This above-outlined difference between $H_2S$-poisoned Catalysts B and C is truly unexpected in view of the fact that the performance of the unpoisoned Catalysts B and C was substantially the same (as indicated by essentially the same "cleanup" temperature at which complete acetylene hydrogenation was achieved and essentially the same "runaway" temperature at which the ethylene/ethane ratio had decreased about 10% from its initial value).

EXAMPLE III

This example illustrates the poisoning effect of an organic disulfide on the performance of two K-promoted Pd/Ag/$Al_2O_3$ catalysts (Catalysts B and C, described in Example I in acetylene hydrogenation).

First, unpoisoned Catalysts B and C were employed in separate acetylene hydrogenation tests, essentially in accordance with the procedure and employing the hydrocarbon feed described in Example II. Then about 2.1 liters of nitrogen stream which had been passed through a bubbler containing liquid dimethyl disulfide (DMDS) was passed at a rate of about 75 cc/minute over Catalyst B and Catalyst C, respectively, at a temperature of 157° F. Thereafter, the reactor tube containing Catalyst B or C was purged overnight with hydrogen gas at a rate of about 100 cc/minute, at a pressure of about 50 psig and a temperature of about 155 ° F. The acetylene hydrogenation test (in accordance with the procedure described in Example I) was then carried with the DMDS-poisoned catalysts. Pertinent test results are summarized in Table II.

TABLE II

| Catalyst | DMDS-Poisoned | Reaction Temp. (°F.) | Mol-% Acetylene in Product | Ethylene/Ethane Mol-Ratio in Product |
|---|---|---|---|---|
| B | No | 160 | 0.003 | 3.69 |
| B | Yes | 155 | 0.207 | 3.71 |
|   |     | 203 | 0.018 | 3.71 |
|   |     | 221 | 0.010 | 3.69 |
|   |     | 239 | 0.008 | 3.63 |
|   |     | 261 | 0.002 | 3.57 |
|   |     | 295 | ~0 | 3.33 |
| C | No | 159 | 0 | 3.69 |
| C | Yes | 155 | 0.160 | 3.70 |
|   |     | 203 | 0.003 | 3.67 |
|   |     | 209 | 0 | 3.66 |
|   |     | 235 | 0 | 3.60 |
|   |     | 258 | 0 | 3.48 |
|   |     | 281 | 0 | 3.36 |
|   |     | 305 | 0 | 3.23 |

Test data in Table II demonstrate that Catalyst C (KF promoted Pd/Ag/$Al_2O_3$) which had been exposed to (poisoned by) dimethyl disulfide (DMDS) performed significantly better as a selective acetylene hydrogenation catalyst than DMDS-poisoned Catalyst B (KOH-promoted Pd/Ag/$Al_2O_3$), as indicated by the differences in cleanup temperature (209° F. for DMDS-poisoned Catalyst C versus 295° F. for DMDS-poisoned Catalyst B) and the ethylene/ethane ratio at the cleanup temperature (3.66 for DMDS-poisoned Catalyst C versus less than 3.57 for DMDS-poisoned Catalyst B).

EXAMPLE IV

This example illustrates the poisoning effect of $H_2S$ on the performance of two K-promoted Pd/$Al_2O_3$ catalysts (without Ag; Catalysts D and E, described in Example I).

The tests were carried out substantially in accordance with the procedure described in Example II. About 900 cc of the $N_2/H_2S$ gas mixture containing 1 volume-% $H_2S$ was passed over Catalyst D and E, respectively. Test results are summarized in Table III.

TABLE III

| Catalyst | H₂S-Poisoned | Reaction Temp. (°F.) | Mol-% Acetylene in Product | Ethylene/Ethane Mol-Ratio in Product |
|---|---|---|---|---|
| D | No | 113 | 0.206 | 3.64 |
|   |    | 129 | 0.173 | 3.66 |
|   |    | 147 | 0.021 | 3.66 |
|   |    | 151 | 0.003 | 3.64 |
|   |    | 155 | 0     | 3.61 |
|   |    | 171 | 0     | 3.54 |
|   |    | 196 | 0     | 3.37 |
|   |    | 217 | 0     | 3.08 |
| D | Yes | 278 | 0.005 | 3.06 |
|   |     | 284 | 0.005 | 3.02 |
|   |     | 306 | 0.004 | 2.92 |
|   |     | 323 | 0.005 | 2.92 |
| E | No | 144 | 0.011 | 3.63 |
|   |    | 145 | 0     | 3.61 |
|   |    | 151 | 0     | 3.56 |
|   |    | 171 | 0     | 3.36 |
|   |    | 208 | 0     | 2.58 |
| E | Yes | 170 | 0.004 | 3.61 |
|   |     | 200 | 0     | 3.50 |
|   |     | 220 | 0     | 3.39 |
|   |     | 254 | 0     | 3.06 |
|   |     | 293 | 0     | 2.51 |

Test data in Table III demonstrate that the H₂S-poisoned Catalyst D (KOH-promoted Pd/Al₂O₃) had become ineffective in catalyzing the complete hydrogenation of acetylene (at temperatures of 278° C. and above), whereas in the case of H₂S-poisoned Catalyst E (KF-promoted Pd/Al₂O₃), complete selective acetylene hydrogenation to ethylene with relatively little hydrogenation of ethylene to ethane (as evidenced by a relatively high ethylene/ethane ratio) was accomplished at about 200° C. These test results (obtained with K-promoted Pd/Al₂O₃ catalysts) confirm the results obtained in Example II with K-promoted Pd/Ag/Al₂O₃ catalysts.

Reasonable variations, modifications and adaptations for various usages and conditions can be made within the scope of the disclosure and the appended claims, without departing from the scope of this invention.

That which is claimed:

1. A catalyst composition which consists essentially of at least one palladium component selected from the group consisting of palladium metal and palladium oxide, at least one alkali metal fluoride and an inorganic support material.

2. A catalyst composition in accordance with claim 1, wherein said at least one alkali metal fluoride is potassium fluoride.

3. A catalyst composition in accordance with claim 1, wherein the palladium content is about 0.01–1 weight-% Pd and the fluorine content is about 0.05–1.5 weight-% F.

4. A catalyst composition in accordance with claim 1, wherein said inorganic support material is selected from the group consisting of alumina, titania, zirconia and mixtures thereof.

5. A catalyst composition in accordance with claim 4, wherein said inorganic support material is alumina.

6. A catalyst composition in accordance with claim 1, wherein the palladium content is about 0.01–1 weight-% Pd, the fluorine content is about 0.05–1.5 weight-% F, and said inorganic support material is selected from the group consisting of alumina, titania, zirconia and mixtures thereof.

7. A catalyst composition in accordance with claim 6, wherein said inorganic support material is alumina.

8. A catalyst composition in accordance with claim 6, wherein said at least one alkali metal fluoride is potassium fluoride.

9. A catalyst composition in accordance with claim 8, wherein said inorganic support material is alumina.

10. A composition in accordance with claim 1, wherein the atomic ratio of fluorine to palladium is about 3:1 to about 30:1.

11. A catalyst composition in accordance with claim 10, wherein the palladium content is about 0.01–1 weight-% Pd and the fluorine content is about 0.05–1.5 weight-% F.

12. A catalyst composition in accordance with claim 11, wherein said at least alkali metal fluoride is potassium fluoride.

13. A catalyst composition in accordance with claim 11, wherein said inorganic support material is selected from the group consisting of alumina, titania, zirconia and mixtures thereof.

14. A catalyst composition in accordance with claim 13, wherein said inorganic support material is alumina.

15. A catalyst composition in accordance with claim 14, wherein said at least one alkali metal fluoride is potassium fluoride.

16. A catalyst composition in accordance with claim 1, having a surface area of about 1–100 m²/g.

17. A catalyst composition in accordance with claim 1, consisting essentially of palladium metal, at least one alkali metal fluoride, and an inorganic support material selected from the group consisting of alumina, titania, zirconia and mixtures thereof.

18. A catalyst composition in accordance with claim 17, wherein said at least one alkali metal fluoride is potassium fluoride and said inorganic support material is alumina.

19. A catalyst composition in accordance with claim 1, consisting essentially of palladium oxide, at least one alkali metal fluoride, and an inorganic support material selected from the group consisting of alumina, titania, zirconia and mixtures thereof.

20. A catalyst composition in accordance with claim 19, wherein said at least one alkali metal fluoride is potassium fluoride and said inorganic support material is alumina.

* * * * *